United States Patent
Suri et al.

(10) Patent No.: US 12,364,444 B2
(45) Date of Patent: Jul. 22, 2025

(54) SYSTEMS AND METHODS FOR AUTOMATED ANALYSIS OF AIRWAY IMAGING

(71) Applicant: Velmeni, Inc., Sunnyvale, CA (US)

(72) Inventors: Mini Suri, Orlando, FL (US); Mohammed El Amine Mokhtari, Mons (BE); Alan Friedel, Hollywood, FL (US); Prashant P. Jaju, Bhopal (IN); Maxine Feinberg, Westfield, NJ (US); Nodesh Shyamsunder, Jacksonville, FL (US); Elias Ennadifi, Mons (BE); Marcus Prümmer, Pegnitz (DE)

(73) Assignee: VELMENI, INC., Sunnyvale, CA (US)

( * ) Notice: Subject to any disclaimer, the term of this patent is extended or adjusted under 35 U.S.C. 154(b) by 0 days.

(21) Appl. No.: 18/749,092

(22) Filed: Jun. 20, 2024

(65) Prior Publication Data
US 2024/0415474 A1    Dec. 19, 2024

Related U.S. Application Data

(60) Provisional application No. 63/661,320, filed on Jun. 18, 2024, provisional application No. 63/521,797, filed on Jun. 19, 2023.

(51) Int. Cl.
*A61B 6/03* (2006.01)
*A61B 6/00* (2024.01)
(Continued)

(52) U.S. Cl.
CPC ............... *A61B 6/032* (2013.01); *A61B 6/50* (2013.01); *A61B 6/5223* (2013.01);
(Continued)

(58) Field of Classification Search
CPC ............... G06T 7/0012; G06T 7/11; G06T 2207/10081; G06T 2207/30061;
(Continued)

(56) References Cited

U.S. PATENT DOCUMENTS 10,932,890 B1   3/2021   Sant et al.
10,937,108 B1   3/2021   Tabak et al.
(Continued)

OTHER PUBLICATIONS

International Search Report issued by the ISA/US in connection with International Application No. PCT/US2023/029755, dated Oct. 27, 2023.
(Continued)

*Primary Examiner* — Aaron W Carter
*Assistant Examiner* — Courtney Joan Nelson
(74) *Attorney, Agent, or Firm* — George Likourezos; Carter, DeLuca & Farrell LLP (57) ABSTRACT

A system for automated image analysis includes an imaging device configured to capture input data of a patient, a processor, and a memory coupled to the processor. The memory has instructions stored thereon, which when executed by the processor, cause the system to: capture input data from the imaging device, the input data including a three-dimensional (3D) image of a portion of a patient; receive the input data from the imaging device; generate a first 3D mask based on the input data; generate a second 3D mask based on the first 3D mask; and determine a diagnostic prediction based on the first 3D mask and the second 3D mask. Generating the second 3D mask includes predicting a plurality of two-dimensional (2D) slices based on the first 3D mask, such that each 2D slice of the plurality of 2D slices is an axial cross-section of the first 3D mask.

17 Claims, 7 Drawing Sheets

(51) Int. Cl.
*A61B 6/50* (2024.01)
*G06T 7/00* (2017.01)
*G06T 7/174* (2017.01)
*G06V 10/82* (2022.01)

(52) U.S. Cl.
CPC ............ *G06T 7/0012* (2013.01); *G06T 7/174* (2017.01); *G06V 10/82* (2022.01); *G06T 2207/10081* (2013.01); *G06T 2207/20081* (2013.01); *G06V 2201/03* (2022.01)

(58) Field of Classification Search
CPC .................. G06T 7/62; G06T 2210/41; G06T 2207/30101; G06T 2207/20076; G06T 2207/30196; G06T 2207/30004; G06T 7/13; G06T 7/174; G06T 7/00; G06T 7/32; G06T 15/08; G06T 7/337; G06T 7/12; G06T 2207/10076; G06T 17/00; G06T 5/92; G06T 2207/20081; G16H 30/40; G16H 50/20; G16H 30/20; G16H 50/30; A61B 6/032; A61B 6/5217; A61B 6/4085; A61B 6/465; A61B 6/50; A61B 6/5223; G06V 2201/031; G06V 2201/03; G06V 20/64; G06V 20/647; G06V 10/26; G06V 10/82

See application file for complete search history.

(56) References Cited

U.S. PATENT DOCUMENTS

| | | | |
|---|---|---|---|
| 10,984,529 B2 | 4/2021 | Carter et al. | |
| 10,991,091 B2 | 4/2021 | Ezhov et al. | |
| 11,158,046 B2 | 10/2021 | Jelicich et al. | |
| 11,189,028 B1 | 11/2021 | Kearney et al. | |
| 11,217,350 B2 | 1/2022 | Kearney et al. | |
| 11,276,151 B2 | 3/2022 | Kearney et al. | |
| 11,311,247 B2 | 4/2022 | Kearney et al. | |
| 11,348,237 B2 | 5/2022 | Kearney et al. | |
| 11,357,604 B2 | 6/2022 | Kearney et al. | |
| 11,366,985 B2 | 6/2022 | Kearney et al. | |
| 11,367,188 B2 | 6/2022 | Kearney et al. | |
| 11,398,013 B2 | 7/2022 | Kearney et al. | |
| 2007/0049840 A1* | 3/2007 | Odry .................... | G16H 30/40 600/532 |
| 2008/0292046 A1* | 11/2008 | Camus ................. | A61B 6/4417 378/4 |
| 2012/0082358 A1* | 4/2012 | Kiraly ...................... | G06T 7/12 382/131 |
| 2019/0216409 A1 | 7/2019 | Zhou et al. | |
| 2019/0220701 A1* | 7/2019 | Novak ................ | G06F 18/2113 |
| 2019/0222176 A1 | 7/2019 | Khlat | |
| 2020/0066391 A1 | 2/2020 | Sachdeva et al. | |
| 2020/0122261 A1 | 4/2020 | Knoener et al. | |
| 2020/0146646 A1 | 5/2020 | Tuzoff et al. | |
| 2020/0175681 A1 | 6/2020 | Ezhov et al. | |
| 2020/0193603 A1* | 6/2020 | Golden .................. | G06T 7/149 |
| 2020/0195903 A1* | 6/2020 | Komp ................... | A61B 1/0661 |
| 2020/0305808 A1 | 10/2020 | Ezhov et al. | |
| 2020/0320751 A1* | 10/2020 | Siemionow ............... | G06T 7/11 |
| 2020/0342539 A1 | 10/2020 | Doney | |
| 2021/0073977 A1 | 3/2021 | Carter et al. | |
| 2021/0074061 A1 | 3/2021 | Brown et al. | |
| 2021/0074425 A1 | 3/2021 | Carter et al. | |
| 2021/0217170 A1 | 7/2021 | Ezhov et al. | |
| 2021/0224919 A1 | 7/2021 | Tabak et al. | |
| 2021/0233233 A1 | 7/2021 | Jelicich et al. | |
| 2021/0272287 A1* | 9/2021 | Neumann .................. | G06T 7/11 |
| 2021/0327000 A1 | 10/2021 | Tabak et al. | |
| 2021/0338387 A1 | 11/2021 | Inam et al. | |
| 2021/0343400 A1 | 11/2021 | Inam et al. | |
| 2021/0383480 A1 | 12/2021 | Tabak et al. | |
| 2021/0390775 A1* | 12/2021 | Ratner ................... | G06N 20/00 |
| 2022/0084267 A1 | 3/2022 | Ezhov et al. | |
| 2022/0189611 A1 | 6/2022 | Farkash et al. | |
| 2022/0192590 A1 | 6/2022 | Hillen | |
| 2022/0277572 A1* | 9/2022 | Fang ...................... | G06V 10/82 |
| 2022/0301717 A1* | 9/2022 | Xia ....................... | G06V 40/174 |

OTHER PUBLICATIONS

Szu-Yin Lin, et al., "Tooth Numbering and Condition Recognition on Dental Panoramic Radiograph Images Using CNNs", IEEE Access, pp. 1-28, Dec. 15, 2021.

F. Baan, et al., "Fusion of intra-oral scans in cone-beam computed tomography scans", Clinical Oral Investigations, pp. 1-9, 2021.

International Search Report and Written Opinion issued by the ISA/US in connection with International Application No. PCT/US2024/034803, dated Aug. 26, 2024.

* cited by examiner

Axial　　　　　　　　Sagittal　　　　　　　　Coronal

SYSTEMS AND METHODS FOR AUTOMATED ANALYSIS OF AIRWAY IMAGING

CROSS-REFERENCE TO RELATED APPLICATION AND CLAIM OF PRIORITY

This application claims the benefit of, and priority to, U.S. Provisional Patent Application No. 63/661,320, filed on Jun. 18, 2024, and U.S. Provisional Patent Application No. 63/521,797, filed on Jun. 19, 2023, the entire contents of which are hereby incorporated herein by reference.

TECHNICAL FIELD

The present application relates to systems and methods for airway imaging analysis, and, more specifically, to a system and method for automated analysis of airway imaging, which utilizes artificial intelligence.

BACKGROUND

Cone-beam computer tomography (CBCT) scanning is a versatile medical imaging technique that produces high resolution, three-dimensional (3D) images of the body. Unlike traditional CT scans that use a fan-shaped X-ray beam, a CBCT scan uses a cone-shaped X-ray beam. The level of detail in a CBCT scan enables accurate measurement of features, helping to identify tissue problems and to detect lesions. As such, CBCT scanning is often configured to show bone, nerves, and soft tissues. The large amount of data and detail provided by CBCT scans can be challenging for a human to process, as the potential issues and/or diseases to be identified require a considerable amount of analysis. Moreover, such analysis must be applied with consistency and attention, posing significant overhead for a human scan reader.

Accordingly, there is a need for an improved, automated analysis of CBCT scans.

SUMMARY

In accordance with aspects of the present disclosure, a system for automated image analysis includes an imaging device configured to capture input data of a patient, a processor, and a memory coupled to the processor. The memory has instructions stored thereon, which when executed by the processor, cause the system to: capture input data from the imaging device, the input data including a three-dimensional (3D) image of a portion of a patient; receive the input data from the imaging device; generate a first 3D mask based on the input data; generate a second 3D mask based on the first 3D mask; and determine a diagnostic prediction based on the first 3D mask and the second 3D mask. Generating the second 3D mask includes predicting a plurality of two-dimensional (2D) slices based on the first 3D mask, such that each 2D slice of the plurality of 2D slices is an axial cross-section of the first 3D mask In another aspect of the present disclosure, the image may include a cone-beam computer tomography (CBCT) scan.

In yet another aspect of the present disclosure, the CBCT scan may be an image of an airway of the patient.

In a further aspect of the present disclosure, the first 3D mask may be a 3D segmentation mask.

In yet a further aspect of the present disclosure, generating the first 3D mask may include training a first machine learning network to extract at least one feature from the input data through a plurality of convolutional layers.

In another aspect of the present disclosure, extracting the at least one feature from the input data includes downsampling to extract high-level features from the input data.

In yet another aspect of the present disclosure, extracting the at least one feature from the input data may include downsampling to extract high-level features from the input data.

In a further aspect of the present disclosure, the second 3D mask may be a patient-specific 3D segmentation mask.

In yet a further aspect of the present disclosure, generating the patient-specific 3D segmentation mask may include: generating a measurement profile for each 2D slice of the plurality of 2D slices by determining at least one of a maximum diameter, a minimum diameter, or an area of the 2D slice; and assigning a label to each 2D slice of the plurality of 2D slices based on a predetermined threshold.

In another aspect of the present disclosure, determining the diagnostic prediction may include training a second machine learning network to generate at least one prediction regarding the airway of the patient.

In accordance with aspects of the present disclosure, a processor-implemented method for automated image analysis includes: capturing input data from an imaging device, the input data including a three-dimensional (3D) image of a portion of a patient; receiving the input data from the imaging device; generating a first 3D mask based on the input data; generating a second 3D mask based on the first 3D mask; and determining a diagnostic prediction based on the first 3D mask and the second 3D mask. Generating the second 3D mask includes predicting a plurality of two-dimensional (2D) slices based on the first 3D mask, such that each 2D slice of the plurality of 2D slices is an axial cross-section of the first 3D mask.

In an aspect of the present disclosure, capturing the input data from the imaging device may include capturing a cone-beam computer tomography (CBCT) scan of the patient.

In another aspect of the present disclosure, capturing the CBCT scan of the patient may include capturing an image of an airway of the patient.

In yet another aspect of the present disclosure, the method further includes displaying the diagnostic prediction on a display as a 3D overlay of the airway of the patient.

In a further aspect of the present disclosure, generating the first 3D mask may include generating a 3D segmentation mask.

In yet a further aspect of the present disclosure, generating the 3D segmentation mask may include training a first machine learning network to extract at least one feature from the input data through a plurality of convolutional layers.

In an aspect of the present disclosure, extracting the at least one feature from the input data may include downsampling to extract high-level features from the input data.

In another aspect of the present disclosure, generating the second 3D mask may include generating a patient-specific 3D segmentation mask by: generating a measurement profile for each 2D slice of the plurality of 2D slices by determining at least one of a maximum diameter, a minimum diameter, or an area of the 2D slice; and assigning a label to each 2D slice of the plurality of 2D slices based on a predetermined threshold.

In yet another aspect of the present disclosure, determining the diagnostic prediction may include training a second machine learning network to generate at least one prediction regarding the airway of the patient.

In accordance with aspects of the present disclosure, a non-transitory computer readable storage medium includes instructions that, when executed by a computer, cause the computer to perform a method for image analysis, including: capturing input data from an imaging device, the input data including a three-dimensional (3D) image of a portion of a patient; receiving the input data from the imaging device; generating a first 3D mask based on the input data; generating a second 3D mask based on the first 3D mask; and determining a diagnostic prediction based on the first 3D mask and the second 3D mask. Generating the second 3D mask includes predicting a plurality of two-dimensional (2D) slices based on the first 3D mask, such that each 2D slice of the plurality of 2D slices is an axial cross-section of the first 3D mask.

BRIEF DESCRIPTION OF THE DRAWINGS

A better understanding of the features and advantages of the disclosed technology will be obtained by reference to the following detailed description that sets forth illustrative embodiments, in which the principles of the technology are utilized, and the accompanying drawings of which.

DETAILED DESCRIPTION

The present application relates to systems and methods for airway imaging analysis, and, more specifically, to systems and methods for automated analysis of airway imaging, which utilizes artificial intelligence. In particular, the systems and methods herein apply deep learning techniques to the processing of dental images to provide a platform for computer-aided charting and diagnosis.

For the purpose of promoting an understanding of the principles of the present disclosure, reference will now be made to exemplary embodiments illustrated in the drawings, and specific language will be used to describe the same. It will nevertheless be understood that no limitation of the scope of the present disclosure is thereby intended. Various alterations, rearrangements, substitutions, and modifications of the features illustrated herein, and any additional applications of the principles of the present disclosure as illustrated herein, which would occur to one skilled in the relevant art and having possession of this disclosure, are to be considered within the scope of the present disclosure.

CBCT scans contain data describing a three-dimensional (3D) representation of the body. For example, a CBCT scan may represent an image of a portion of a patient's anatomy. CBCT scans are taken for various medical purposes. For example, a practitioner may image a patient's airway to assess an airway and/or vocal cord issue. In another example, a dentist may scan a patient's teeth and gums prior to surgery to map out a surgical plan.

A CBCT scan may be in the format of a 3D data file, such as a NifTI (Neuroimaging Informatics Technology Initiative) file, or a series of two dimensional (2D) files, such as DICOM (Digital Imaging and Communication in Medicine) files. Generally, denser elements are lightest, soft tissues are slightly darker, and voids and/or spaces are darkest. Therefore, before CBCT scans are processed, areas of interest (e.g., a patient's airway) may be indistinctly seen. The system and method disclosed below are used to extract 2D slices from 3D imaging, e.g., CBCT scans, to produce a precise view with shading indicating bodily areas that are dangerously narrow. In doing so, valuable medical information is produced, which is generally not available through conventional image processing.

Figure 1:
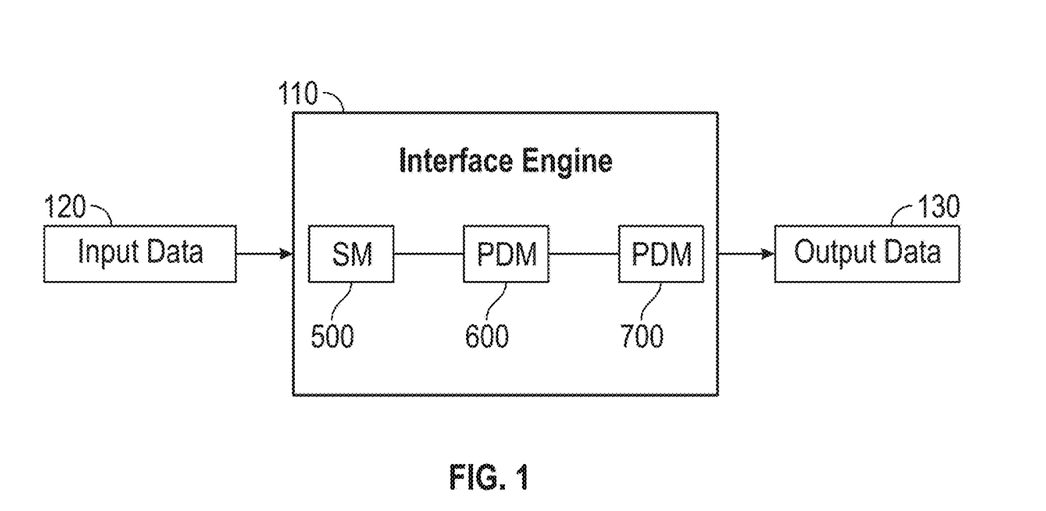
FIG. 1 is an illustration of a system for automated analysis of airway imaging, in accordance with aspects of the present disclosure.

Referring to FIG. 1, there is shown an illustration of an exemplary image analysis system 100 in accordance with aspects of the present disclosure. Image analysis system 100 includes inference engine 110 (e.g., an airway analysis processor), which contains a segmentation module 500, a pathology detection module 600, and a prediction module 700. Inference engine 110 is configured to process input data 120, (e.g., 3D CBCT scan of the body), and produce output data 130 (e.g., a 3D prediction model 710). In doing so, segmentation module 500, pathology detection module 600, and prediction module 700 may operate sequentially to analyze input data 120 and produce output data 130. The results of each analysis may be merged to produce output data 130. As described further below, output data 130 may be in the form of a 3D image indicating features of a patient, such as varying widths of an airway denoting healthy and unhealthy tissue portions. In aspects, output data 130 may be used to provide a recommendation to a patient. A recommendation may include a diagnosis, such as an airway disease to be treated.

As will be described in more detail below, image analysis system 100 may implement statistical models and/or machine learning models (e.g., neural network) that process the input data 120 to automatically learn and identify important features thereof. This provides a benefit over traditional image processing techniques by saving time and resources wasted during manual identification and creation of explanatory features of input data 120. For example, input data 120 may be fed to a machine learning model, such as machine learning network 300 (described below) to perform image segmentation and generate predictive diagnostics, e.g., output data 130.

Figure 2:
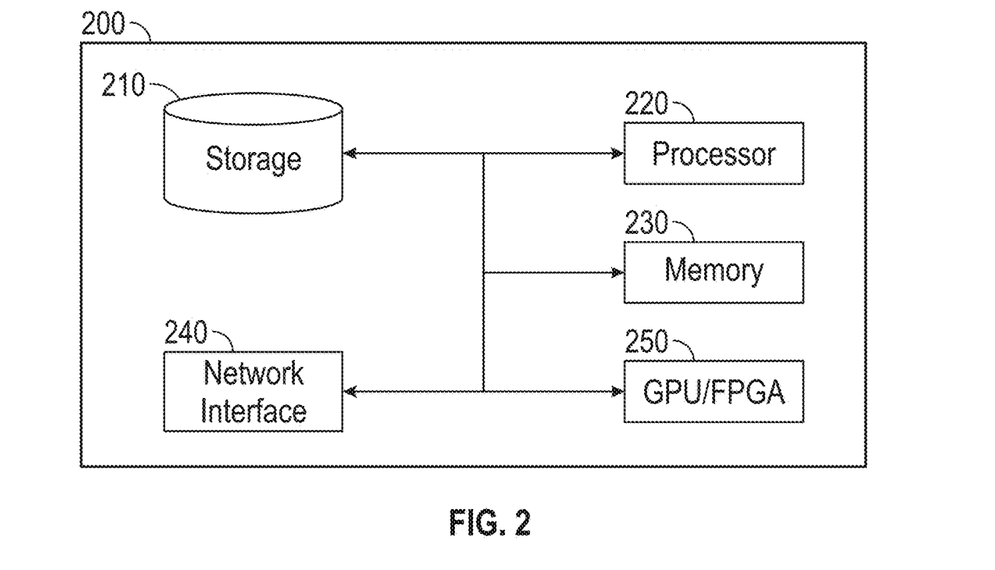
FIG. 2 is a block diagram of exemplary components of a controller of FIG. 1, in accordance with aspects of the present disclosure.

Referring now to FIG. 2, exemplary components of the controller 200 are shown. The controller 200 generally includes a storage or database 210, one or more processors 220, at least one memory 230, and a network interface 240. In aspects, the controller 200 may include a graphical processing unit (GPU) 250, which may be used for processing machine learning network models.

Database 210 can be located in storage. The term "storage" may refer to any device or material from which information may be capable of being accessed, reproduced, and/or held in an electromagnetic or optical form for access by a computer processor. Storage may be, for example, volatile memory such as RAM, non-volatile memory, which permanently holds digital data until purposely erased, such as flash memory, magnetic devices such as hard disk drives, and optical media such as a CD, DVD, and/or Blu-ray Disc™, or the like.

In aspects, data may be stored on the controller 200, including, for example, CBCT scans, patient profiles, and/or other data. The data can be stored in the database 210 and sent via the system bus to the processor 220. The database 210 may store information in a manner that satisfies information security standards and/or government regulations, such as Systems and Organization Controls (e.g., SOC 2), General Data Protection Regulation (GDPR), and/or International Organization for Standardization (ISO) standards.

Processor 220 executes various processes based on instructions that can be stored in the at least one memory 230 and utilizing the data from the database 210. With reference also to FIG. 1, a request from a user device, such as a mobile device or a client computer, can be communicated to the controller 200 through a network interface. The illustration of FIG. 2 is exemplary, and persons skilled in the art will understand that other components may exist in controller 200. Other components are not illustrated for clarity of illustration.

In aspects, other systems, servers, and/or devices not illustrated in FIG. 1 may be included. In embodiments, one or more of the illustrated components may be omitted. Such and other embodiments are contemplated to be within the scope of the present disclosure.

Figure 3:
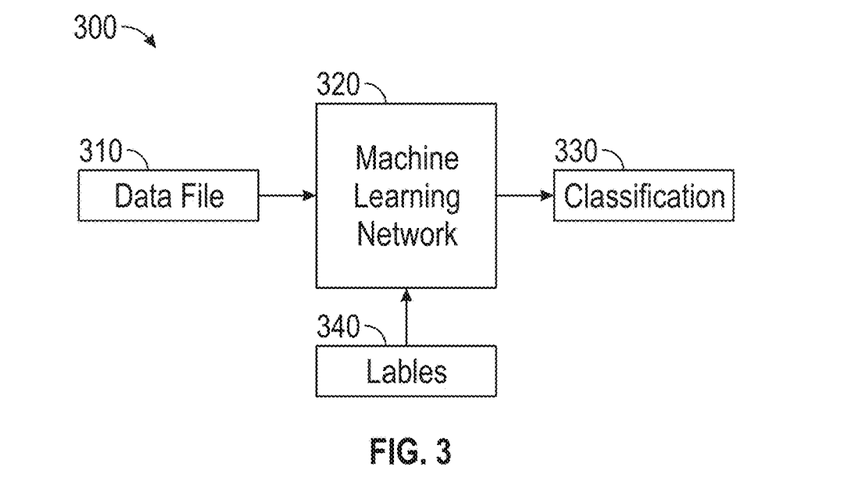
FIG. 3 is a block diagram of a machine learning network with inputs and outputs of a deep learning neural network, in accordance with aspects of the present disclosure.

With reference to FIG. 3, a block diagram for a machine learning network 320 for classifying data in accordance with some aspects of the disclosure is shown. The term "machine learning model" may include, but is not limited to, neural networks, recurrent neural networks (RNN), generative adversarial networks (GAN), decision trees, Bayesian Regression, Naive Bayes, nearest neighbors, least squares, means, and support vector machine, among other data science and machine learning techniques which persons skilled in the art will recognize.

In some systems, a machine learning network 320 may include, for example, a convolutional neural network (CNN), a regression and/or a recurrent neural network. A deep learning neural network includes multiple hidden layers. As explained in more detail below, the machine learning network 320 may leverage one or more classification models 330 (e.g., CNNs, decision trees, a regression, Naive Bayes, and k-nearest neighbor) to classify data. In aspects, the machine learning network 300 (e.g., classification model) may use a data file 310 and labels 340 for classification. The machine learning network 320 may be executed on the controller 200 (FIG. 2). Persons of ordinary skill in the art will understand the machine learning network 320 and how to implement it.

In machine learning, a CNN is a class of artificial neural network (ANN). The convolutional aspect of a CNN relates to applying matrix processing operations to localized portions of data, and the results of those operations (which can involve dozens of different parallel and serial calculations) are sets of many features that are delivered to the next layer. A CNN typically includes convolution layers, activation function layers, deconvolution layers (e.g., in segmentation networks), and/or pooling (typically max pooling) layers to reduce dimensionality without losing too many features. Additional information may be included in the operations that generate these features. Providing unique information, which yields features that give the neural networks information, can be used to provide an aggregate way to differentiate between different data input to the neural networks.

Figure 4:
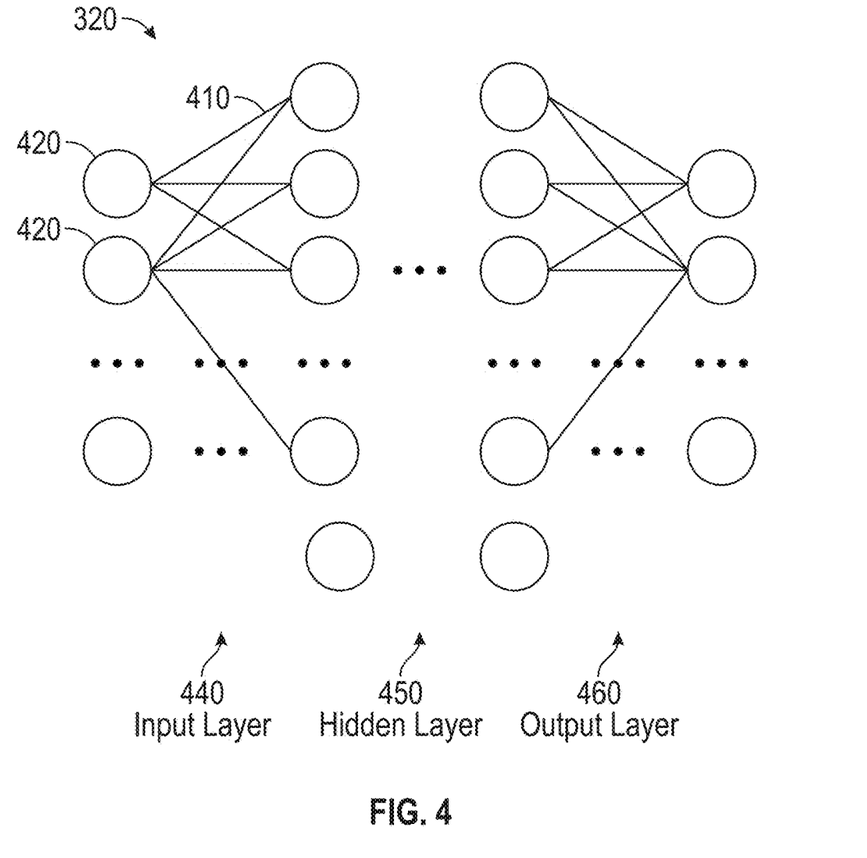
FIG. 4 is a diagram of layers of the machine learning network of FIG. 3, in accordance with aspects of the present disclosure.

Referring to FIG. 4, generally, a machine learning network 320 (e.g., a convolutional deep learning neural network) includes at least one input layer 440, a plurality of hidden layers 450, and at least one output layer 460. The input layer 440, the plurality of hidden layers 450, and the output layer 460 all include neurons 420 (e.g., nodes). The neurons 420 between the various layers are interconnected via weights 410. Each neuron 420 in the machine learning network 320 computes an output value by applying a specific function to the input values coming from the previous layer. The function that is applied to the input values is determined by a vector of weights 410 and a bias. Learning, in the deep learning neural network, progresses by making iterative adjustments to these biases and weights. The vector of weights 410 and the bias are called filters (e.g., kernels) and represent particular features of the input (e.g., a particular shape). The machine learning network 320 may output logits. Although CNNs are used as an example, other machine learning classifiers are contemplated.

The machine learning network 320 may be trained based on labeling training data to optimize weights. For example, samples of feature data may be taken and labeled using other feature data. In some methods in accordance with this disclosure, the training may include supervised learning or semi-supervised. Persons of ordinary skill in the art will understand training the machine learning network 320 and how to implement it.

Figure 5:
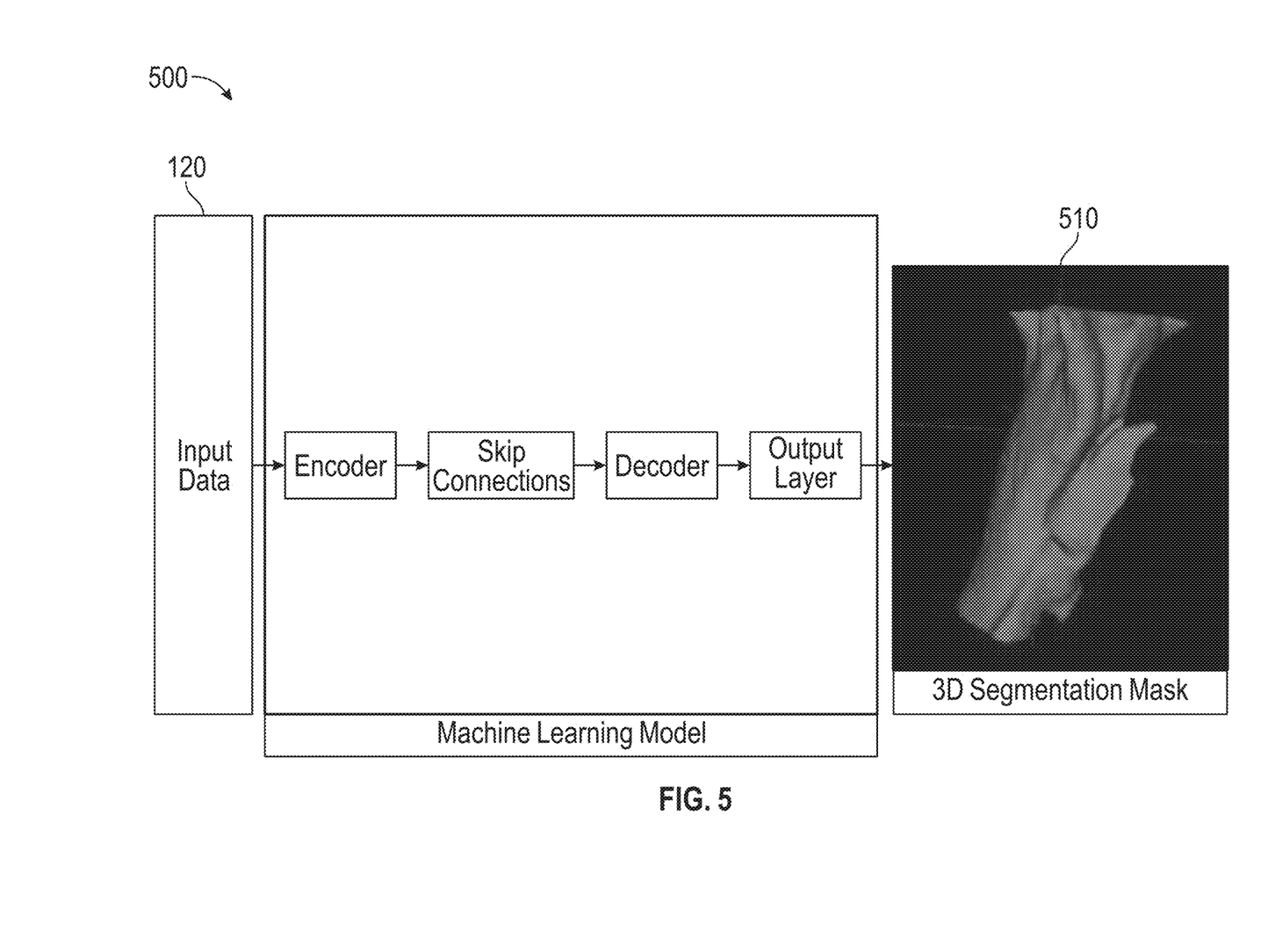
FIG. 5 is an illustration of a segmentation module within the system of FIG. 1, in accordance with aspects of the present disclosure.

Now referring to FIG. 5, segmentation module 500 is configured to identify and segment a portion of input data 120 (e.g. specific structures or tissues) to produce a 3D segmentation mask 512 (e.g., a first 3D mask). Segmentation module 500 may receive input data 120 in the form of an image. For example, segmentation module 500 may receive a scan of a patient's airway as a CBCT image. Input data 120 may be a 3D file and/or a set of 2D files. Input data 120 may be resized prior to processing through segmentation module 500. In aspects, input data 120 may be truncated CBCT data, e.g., a lower portion of the airway may be cropped in the field of view of the CBCT, where the pathological section of the airway is still visible.

As portions of input data 120 (e.g., an airway) may not be consistent in shape and/or size, a simple side view in a vertical cross-section is not an optimal method to analyze data features. For example, an airway is typically irregularly shaped, thus a side view will not accurately depict a width (e.g., "openness") of the airway. To solve this problem, a machine learning model extracts features through a series of convolutional layers of input data 120, e.g., volume data via 3D convolutional layers. This provides a benefit over traditional image processing techniques, as the 3D input data 120 may be processed as a whole within a seconds (e.g., 2-5 seconds), without first extracting individual 2D layers for analysis, which may be time and resource intensive for segmentation module 500.

The machine learning model may be machine learning network 300, although various type of machine learning models are contemplated. Generally, the machine learning model is a custom deep neural network (DNN) model, which generally uses a 3D encoder and a decoder with shortcuts. The encoder may be configured to extract features through the convolutional layers. For example, each convolutional layer typically contains binary values processed by the machine learning model (i.e., logical 0 and 1 numerals representative of image segments). The "0" values may represent the background of an image, and "1" values may represent the foreground, e.g., the area of interest, such as the airway. In aspects, the DNN model may be a 3D convolutional neural networks (CNN), which offers advantages over other machine learning models for extract features from 3D images. For example, unlike traditional 2D CNNs, 3D CNNs provide the benefit of 3D convolutional filters that can simultaneously process depth, height, and width. This enables the network to capture spatial relationships and context within the volume, which is crucial for understanding 3D structures.

During extraction, segmentation module 500 downsampling may be used to progressively extract features from low-level (e.g., edges and textures) to high-level (e.g., shapes and objects) abstractions, thereby performing a multilevel analysis. Different methods of downsampling may be used. For example, the encoder may first accept a $256^3$ input size segmentation layer, which is processed to extract finer details in input data 120 such as etching. Thereafter, the encoder may downsample the segmentation later input by a factor of 2, e.g., a $128^3$ input size, $64^3$ input size, and/or $32^3$ input size, where more globally-based features are extracted with each down sample in the input size of the segmentation layer. At each level, the encoder may implement an activation function and a normalization function. The activation function is configured to recognize complex patterns in the segmentation layers (e.g., Leaky ReLU, Rectified Linear Unit (ReLU), Sigmoid, and/or Exponential Linear Unit (ELU)). For example, Leaky ReLU may be utilized to address the "dying ReLU" problem by allowing a small, non-zero gradient when the unit is not active (i.e., x<0), which is represented as follows:

$$LeakyReLu(x) = \begin{cases} x & \text{if } x > 0 \\ ax & \text{if } x \leq 0 \end{cases} \text{ where } \alpha \text{ is a small constant}$$

The normalization function is configured to standardize the input data and/or intermediate activations to improve training efficiency and model performance (e.g., batch normalization (BN), layer normalization (LN), and/or instance normalization (IN)). For example, batch normalization may be utilized to standardize the activations of each layer across mini-batches during training. Prior to the decoder, skip connections may be employed.

The decoder is configured to produce segmented output (e.g., an output layer) using the features extracted by the encoder. In doing so, segmentation module 500 concatenates the extracted features to produce a dense pixel mask 510 (e.g., a concatenation layer). For example, decoder may generate a 256 binary pixel mask. Once image segmentation is complete, segmentation module 500 may output a 3D segmentation mask 512 (e.g., concatenation layer). 3D segmentation mask 512 contains the pixels of input data 120 representing the area of interest 1 to be segmented from the background 0 (e.g., an organ within a 3D scan, such as an airway).

After processing, the 3D segmentation mask 512 may undergo smoothing and/or rendering to produce a 3D mesh. As used herein, a smoothing operation generally refers to a computational process used to reduce noise, remove small artifacts, and/or create a more visually and functionally appealing surface in 3D volumetric data. For example, smoothing may enhance the quality of segmented regions in the 3D segmentation mask 512, making a 3D output mesh more suitable for visualization and subsequent analysis. The final 3D mesh may be used by a clinician for realization of the surface of the body part of the patient, e.g., the airway.

In aspects, segmentation module 500 may also process individual 2D slices of 3D input data, dependent upon the analysis required. The shape and/or size of each 2D slice may differ from scan to scan based on the imaging methods, location, and/or machinery used. Typical sizes of 2D slices are 256×256 pixels and 512×512 pixels. Similar to the above-mentioned layers, each 2D slice may be composed of binary values, e.g., 0 and 1 values.

With reference to FIGS. 8A-8F, examples of input data 120 and 3D segmentation mask 512 are shown. FIG. 8A represents input data 120 showing a horizontal cross section of a patient's head and/or airway, e.g., an axial view. FIG. 8B represents 3D segmentation mask 512 showing the processed version of FIG. 8A. As shown from the lighter shading, the area of interest 0 is the airway located in a central portion of the scan. FIG. 8C represents input data 120 showing a side view of the patient's head and/or airway, e.g., a sagittal view. FIG. 8D represents 3D segmentation mask 512 showing the processed version of FIG. 8C. As shown from the lighter shading, the area of interest 0 is the airway located in a central portion cascading vertically down the scan with varying degrees of narrowing. FIG. 8E represents input data 120 showing a coronal view of a patient's head and/or airway. FIG. 8F represents segmentation mask 312 showing the processed version of FIG. 8E. As shown from the lighter shading, the area of interest 0 is in a smaller, central to upper portion of the scan with a consistent width.

Figure 6:
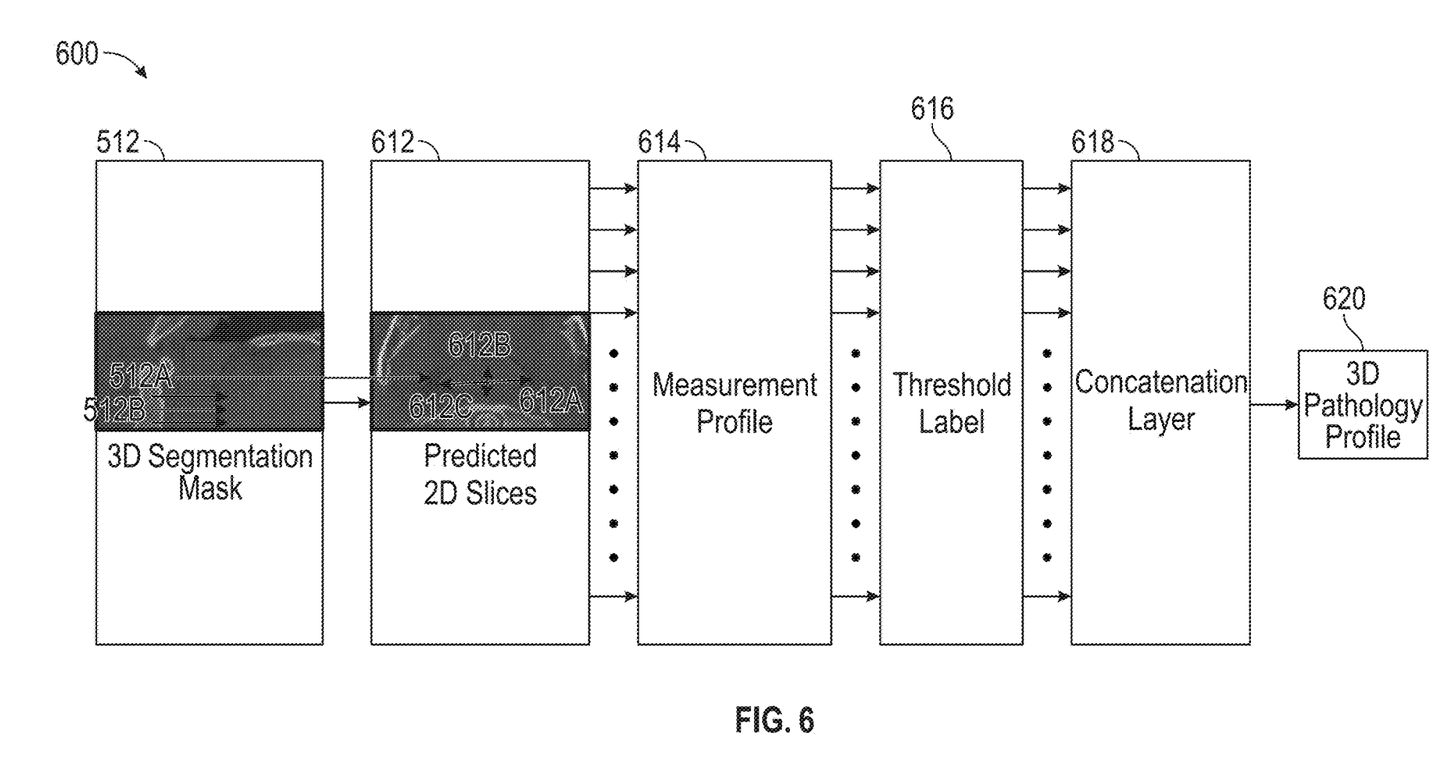
FIG. 6 is an illustration of a pathology detection module within the system of FIG. 1, in accordance with aspects of the present disclosure.

Now referring to FIG. 6, pathology detection module 600 is configured to process 3D segmentation mask 512 and produce a 3D pathology profile 620 (e.g., a second 3D mask). To do so, diameters and/or areas are calculated for each axially oriented cross-section of 3D segmentation mask 512. Generally, the cross-sections of 3D segmentation mask 512 are sampled in short distances dependent on the slice resolution of the input data 120. For example, there may be approximately 0.2 mm spacing between each cross-section, although larger and/or smaller spacing values are contemplated.

Initially, a cross section 512A through the long axis of 3D segmentation mask 512 is input to calculate a cross-section in an axial direction, e.g., a predicted 2D slice 612. Next, inside the predicted 2D slice 612, a maximum diameter 612A and a minimum diameter 612B of the area of interest are calculated (e.g., an airway), to produce a cross-sectional airways measurement profile. Next, further cross-section(s) 512B along the long axis of 3D segmentation mask 512 are input to calculate an airway area cross-section (e.g., another predicted 2D slice 612), which is used to calculate an airways area 612C and further determine an area profile, e.g., a created airways diameter.

The cross-sectional airways profile and/or the area profile form the measurement profile 614. Pathologic sections of 3D segmentation data 512 are detected by analysis of the measurement profile 614 along each cross-section (e.g., each predicted 2D slice) using predetermined threshold values. If a thickness of a cross-section is below the predetermined threshold value, the cross section receives a first threshold label 616. For example, a cross-section thinner than 10 mm may be labeled as narrowing or constricting, e.g., a narrowing section. If a thickness of a cross-section exceeds the predetermined threshold value, the cross-section receives a second threshold label 616. For example, a cross-section thicker than 10 mm may be labeled as wide or healthy, e.g., a normal cross-section. In aspects, the narrowing sections may be detected using shape analysis of the measurement profile 614.

In aspects, additional labels and/or thresholds may be used. For example, three labels may be applied to three different width ranges of each cross-section. Pathology detection module 600 may assign one of three categories: "Normal," which is between 8-25 mm in width, "Warning" which is between 5-7.99 mm in width, and "Danger," which is between 1-4.99 mm in width, although various other ranges are contemplated. The width may include and/or be based on a diameter within measurement profile 614, such as the maximum diameter.

The width may be calculated using a two-step process. First, pathology detection module 600 determines a number of voxels that represent the width, (e.g., a 3D equivalent of the pixels in each predicted 2D slice 612). For example, a set of voxels may represent a volume, e.g., width of scanned tissues. Second, pathology detection module 600 determines the width in millimeters by multiplying the number of determined voxels by the voxel's true dimensions (e.g., the width and/or thickness of each individual voxel). For example, a typical CT scan might have a slice thickness of 1 mm and an in-plane resolution of 0.5 mm×0.5 mm, resulting in a voxel size of 0.5 mm×0.5 mm×1 mm.

Pathology detection module 600 determines a start and end point of the narrowing and/or constricting cross-sections based on the measurement profile 614. The narrowing cross-sections may then be visualized and/or highlighted in 3D. Layers, e.g., concatenation layers 618 of each cross-section (e.g., each predicted 2D slice) are then combined to produce a 3D pathology profile 620, e.g., a patient-specific 3D segmentation mask. In aspects, 3D rendering and/or color maps may be used to visualize features, e.g., different diameters in the narrowing section of the patient's airway. For example, blue may represent wider regions, purple may represent warning regions, ad red may indicate warning, e.g., narrowing regions of the airway.

Figure 7:
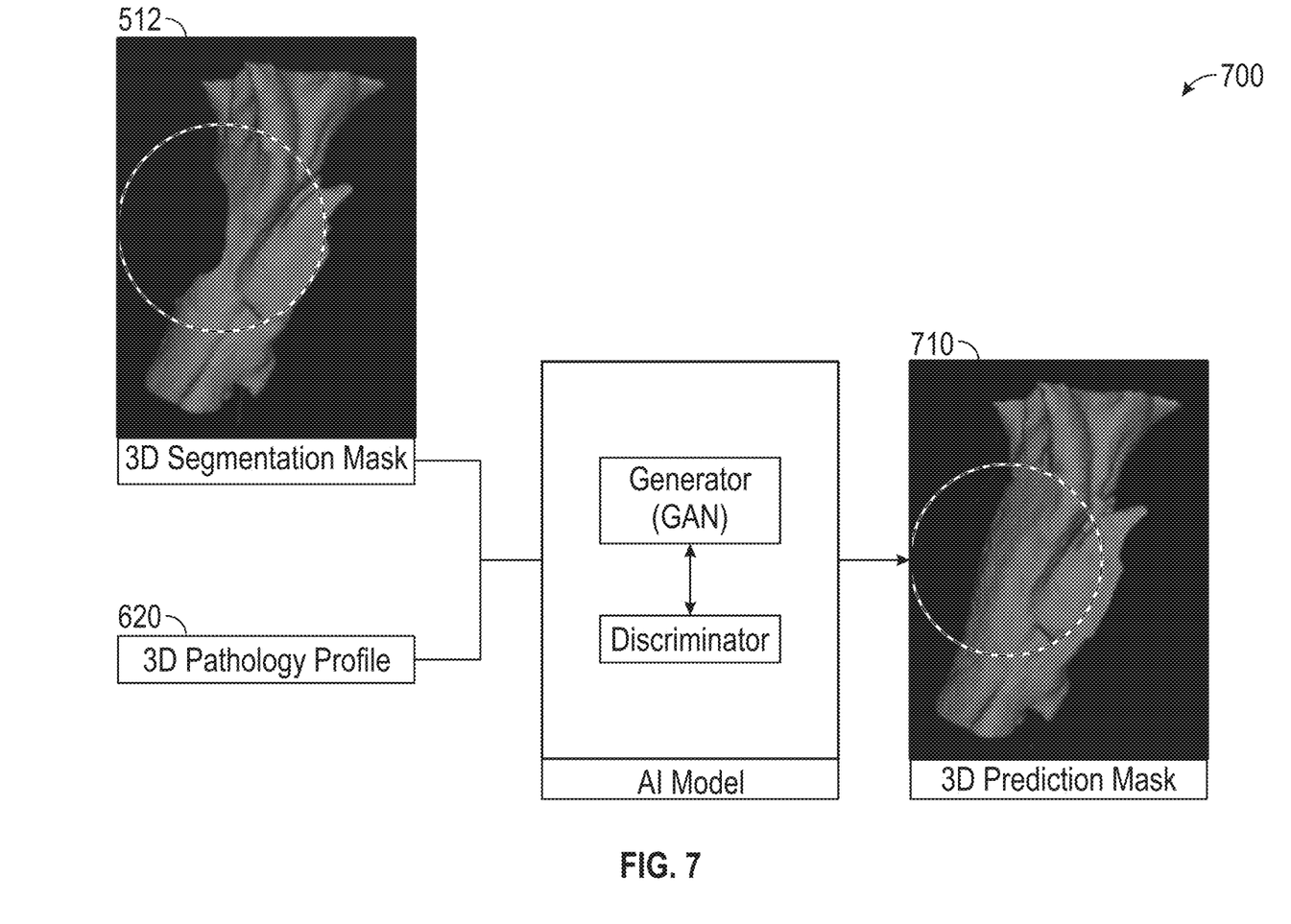
FIG. 7 is an illustration of a prediction module within the system of FIG. 1, in accordance with aspects of the present disclosure.

Now referring to FIG. 7, prediction module 700 is configured to generate a 3D prediction model 710 (e.g., a diagnostic prediction) using a machine learning model, which is rendered to produce the final output data 130. The 3D prediction model 710 shows a visualization of predicted normal pathology after treatment, which is based on an enlarged version of the pathology provided in pathology profile 620.

For example, the 3D prediction model 710 may show predicted enlarged airways of a patient after surgery. The machine learning model may be machine learning network 300, although various types of machine learning models are contemplated. Generally, the machine learning model is a trained generative adversarial network (GAN), which generally uses a convolutional 3D model. The GAN may be trained to generate normal pathology, (e.g., normal airways), based on pathology profile 620. In aspects, the GAN is trained with a second neuronal network, e.g., a discriminator, which tries to distinguish whether data is generated by the GAN or real-world normal pathology.

The GAN and discriminator are trained iteratively. Generally, a custom loss function is utilized to punish the GAN model when normal pathology from pathology profile 620 (e.g., a healthy airway) is mislabeled as narrow, such as by generating altered output to enlarge the pathology. Conversely, the custom loss function may reward the GAN model when narrowed pathology from pathology profile 620 is enlarged in a realistic way. Enlargement may be considered realistic when the discriminator is no longer able to distinguish between data generated by the GAN or real-world pathology. The 3D loss function may use a smoothed binary mask, which masks only narrowed pathology from pathology profile 620 detected by pathology detection module 600. Once trained, the GAN produces the 3D prediction model 710 containing the predicted enlarged pathology, e.g., enlarged airways after potential treatment.

In aspects, the 3D segmentation mask 512 may visualized as an overlay on the 3D prediction model 710 to produce the final output 130, which provides a direct comparison to a clinician for further treatment planning. In aspects, 3D segmentation mask 512 and/or 3D prediction model may be resized and transposed to match the dimensions and orientation, respectively, of input data 120.

Figure 8:
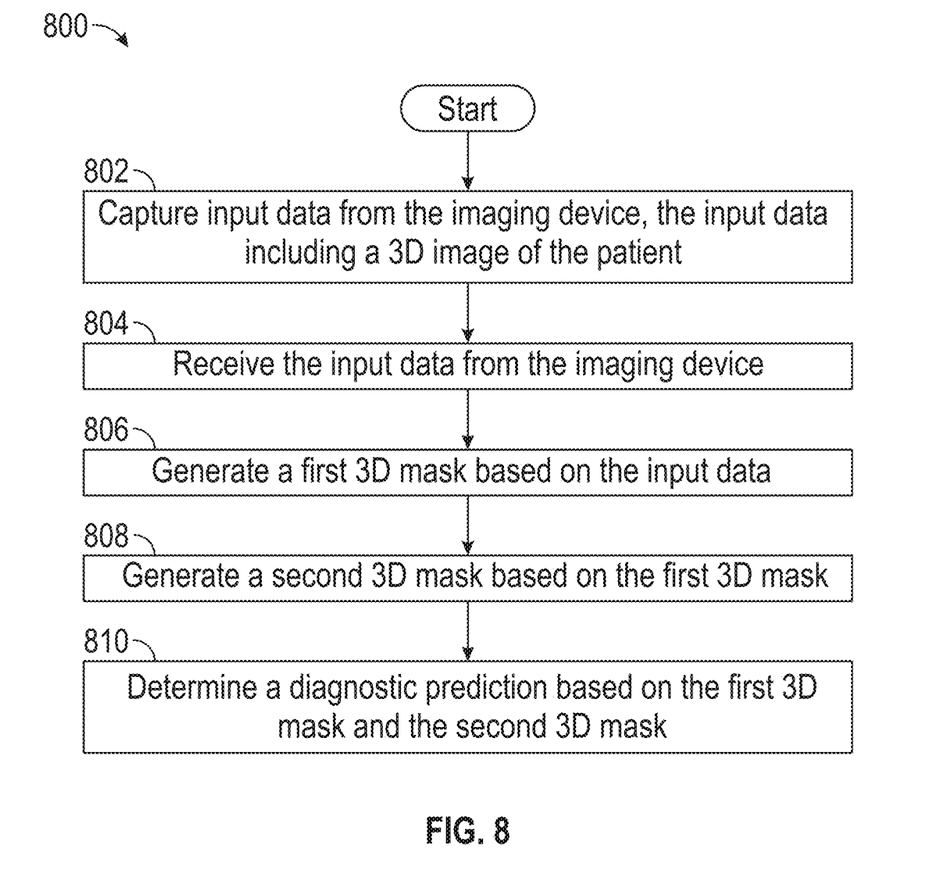
FIG. 8 is a flow diagram of an exemplary use of the system of FIG. 1, in accordance with aspects of the present disclosure.
Figure 9A:
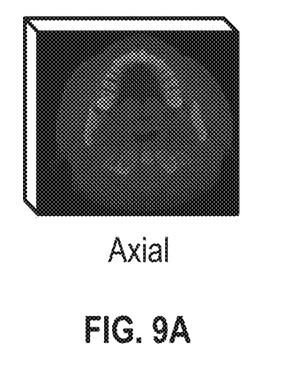
FIGS. 9A-9F illustrate exemplary output from the segmentation module within the system of FIG. 1, in accordance with aspects of the present disclosure.
Figure 9B:
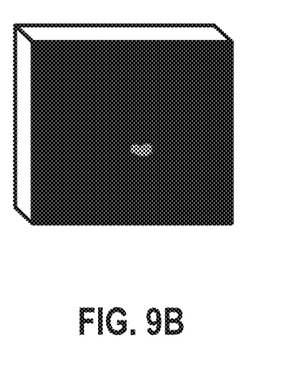
Figure 9C:
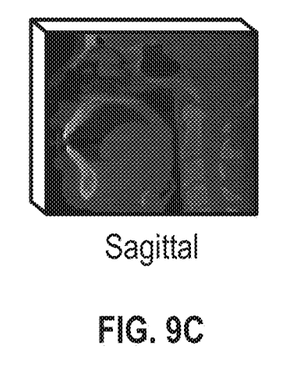
Figure 9D:
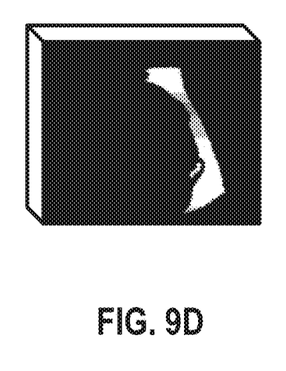
Figure 9E:
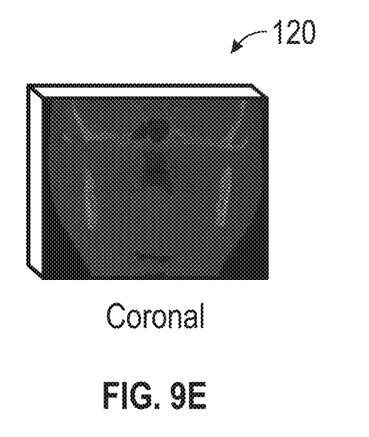
Figure 9F:
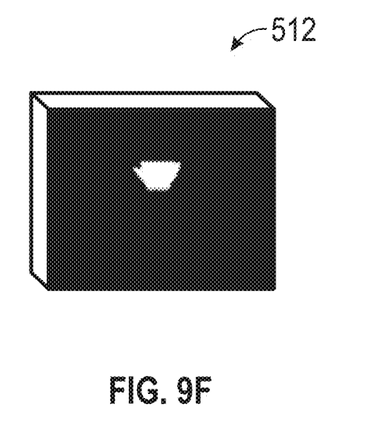

FIG. 8 shows a method 800 for an exemplary use of image analysis system 100. Although the steps of method 800 of FIG. 8 are shown in a particular order, the steps need not all be performed in the specified order, and certain steps can be performed in another order. In various aspects, the method 800 of FIG. 8 may be performed all or in part by controller 200 of FIG. 2. In other aspects, the method 800 of FIG. 8 may be performed all or in part by another device, for example, a mobile device and/or a client computer system. These and other variations are contemplated to be within the scope of the present disclosure.

Initially, at step 802, the controller 200 causes image analysis system 100 to capture input data 120 using an imaging device. Generally, input data is a 3D image, which is stored for future analysis, e.g., in memory 230 of controller 200. For example, a practitioner may perform a CBCT scan of a patient. The CBCT scan may be an axial, sagittal, or coronal view of the patient's airway. Various CBCT scanners known by those skilled in the art may be used including a Carestream CS 9300®, Planmeca ProMax 3D®, i-CAT FLX®, and/or Surona Orthophos SL 3D®. In aspects, alternative imaging may be used, such as x-ray, position emission tomography (PET), PET-CT, ultrasound, fluoroscopy, and/or bronchoscopy imaging.

Next, at step 804, the controller 200 causes image analysis system 100 to receive the input data 120. The input data 120 may be received from a user profile. To do so, the practitioner may select the input data 120 from an existing user profile or create a new user profile including the input data 120. In aspects, the user profile creation process and/or image upload to an existing user profile may occur automatically. For example, after a CBCT scan of a patient's airway is conducted, resulting images may be processed and/or uploaded to a user profile in real time as input data 120.

In aspects, user profile may be uploaded to a network for future access by the practitioner and/or patient. For example, a user profile may contain a dashboard including an imaging tab with past scans, a recommendation tab containing diagnoses and treatment, a prescription tab for obtaining necessary treatment, and/or a messaging tab. The user profile may be accessed on various user devices, including mobile devices, personal computers, laptops, tablets, and/or virtual reality devices.

Next, at step 806, the controller 200 causes image analysis system 100 to generate a first 3D mask, e.g., 3D segmentation mask 512, based on input data 120. Generally, 3D segmentation mask 512 is generated using segmentation module 500.

Segmentation module 500 trains a machine learning network, such as a DNN, including an encoder and decoder. In aspects, the DNN and/or other network may be machine learning network 300. To produce the segmentation mask, the encoder extracts relevant features from input data 120 through convolutional layers. In doing so, downsampling is performed to extract increasingly high-level features from input data 120. For example, at a low level, fine details such as edges and textures may be extracted, at an intermediate level, contours and/or simple shapes may be extracted, and at a high level, specific shapes, patterns, and/or geometries may be extracted. Such features are passed on in data to a decoder, which produces output layers concatenated to generate the resultant 3D segmentation mask 512. In aspects, 3D segmentation mask 512 may undergo a smoothing operation involving techniques like Gaussian smoothing, mean filtering, median filtering, anisotropic diffusion, and/or morphological operations. A resulting 3D output mesh may also be stored in memory 230 for future analysis.

Next, at step 808, the controller 200 causes image analysis system 100 to generate a second 3D mask, e.g., 3D pathology profile 620, based on the 3D segmentation mask 512. Generally, the pathology profile 620 is generated using pathology detection module 600.

The pathology profile 620 may be generated based on predicted 2D slices 612. First, measurement profile 614 is generated by determining at least one of a maximum diameter, a minimum diameter, or an area of each predicted 2D slice 612. A label is assigned to each predicted 2D slice 612 based on a predetermined threshold. For example, if an airway in a slice is narrower than 10 mm, it may be labeled as "narrowing," causing shading on the image where narrowing of the airway is occurring. The predicted 2D slices 612 are then concatenated through concatenation layers 618 to produce the 3D pathology profile 620. For example, pathology detection module 600 may generate a pathology profile 620 indicating color-coordinated airways of a patient indicating narrow and wider regions.

Finally, at step 810, the controller 200 causes image analysis system 100 to determine a diagnostic prediction, e.g., 3D prediction model 710 based on the 3D segmentation mask 512 and the pathology profile 620. Here, the 3D segmentation mask 512 and the pathology profile 620 are input into an AI model, such as a GAN, to show how the narrowed airways of 3D segmentation mask 512 may be enlarged through potential surgery. In doing so, the GAN generates a prediction(s) regarding a width and/or diameter of each portion of the airway. For example, the image analysis system 100 may output an overlay of the 3D segmentation mask 512 and the 3D prediction model 710.

In aspects, the controller causes image analysis system 100 to determine a patient recommendation based on the output data 130. To do so, inference engine 110 may combine the first 3D mask and the second 3D mask, which are generally of the same size and orientation. The recommendation may be a diagnosis for treatment and medication. For example, the scans may automatically process the output data 530 using machine learning to determine a disease such as asthma based on similar patient images.

In aspects, a visual, audio, and/or haptic alert may appear on a user device to indicate various features of the output data 530, such as particularly concerning areas. For example, if an airway is extremely narrow, the screen may flash red and/or indicate an area of concern. The data provided may further be stored in a user profile for future analysis. For example, a clinician may upload the results to a patient chart. The clinician may then reference a new scan as an overlay over an old scan at a future visit to determine any further narrowing of the airway. In aspects, output data 130 may be overlaid over a surgical plan.

While described for use in airway imaging, it will be understood that image analysis system 100 may be implemented for use in various settings. For example, image analysis system 100 may be used for scanning other various bodily organs, such as the lungs, pulmonary values, arteries, and/or other regions of the body.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described methods, programs, algorithms, or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages that are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above are also intended to be within the scope of the disclosure.

What is claimed is:

1. A system for automated image analysis, comprising:
an imaging device;
a processor; and
a memory coupled to the processor, the memory having instructions stored thereon, which when executed by the processor, cause the system to:

capture input data from the imaging device, the input data including a three-dimensional (3D) image of a portion of a patient;
receive the input data from the imaging device;
generate a first 3D mask based on the input data;
generate a second 3D mask based on the first 3D mask, wherein generating the second 3D mask includes generating a patient-specific 3D segmentation mask by:
predicting a plurality of two-dimensional (2D) slices based on the first 3D mask, wherein each 2D slice of the plurality of 2D slices is an axial cross-section of the first 3D mask;
generating a measurement profile for each 2D slice of the plurality of 2D slices by determining a maximum diameter and a minimum diameter of a portion of each 2D slice; and
assigning a label to each 2D slice of the plurality of 2D slices based on a predetermined threshold, wherein the predetermined threshold is based on a thickness of a cross-section of the measurement profile; and
determine a diagnostic prediction based on the first 3D mask and the second 3D mask.

2. The system of claim 1, wherein the 3D image includes a cone-beam computer tomography (CBCT) scan.

3. The system of claim 2, wherein the CBCT scan is an image of an airway of the patient.

4. The system of claim 3, wherein the instructions, when executed by the processor, further cause the system to display the diagnostic prediction on a display as a 3D overlay of the airway of the patient.

5. The system of claim 3, wherein determining the diagnostic prediction includes training a second machine learning network to generate at least one prediction regarding a diameter of the airway of the patient.

6. The system of claim 1, wherein the first 3D mask is a 3D segmentation mask.

7. The system of claim 6, wherein generating the first 3D mask includes training a first machine learning network to extract at least one feature from the input data through a plurality of convolutional layers.

8. The system of claim 7, wherein extracting the at least one feature from the input data includes downsampling to extract high-level features from the input data.

9. A processor-implemented method for automated image analysis, the method comprising:
capturing input data from an imaging device, the input data including a three-dimensional (3D) image of a portion of a patient;
receiving the input data from the imaging device;
generating a first 3D mask based on the input data;
generating a second 3D mask based on the first 3D mask, wherein generating the second 3D mask includes generating a patient-specific 3D segmentation mask by:
predicting a plurality of two-dimensional (2D) slices based on the first 3D mask, wherein each 2D slice of the plurality of 2D slices is an axial cross-section of the first 3D mask;
generating a measurement profile for each 2D slice of the plurality of 2D slices by determining a maximum diameter and a minimum diameter of a portion of each 2D slice; and
assigning a label to each 2D slice of the plurality of 2D slices based on a predetermined threshold, wherein the predetermined threshold is based on a thickness of a cross-section of the measurement profile; and
determining a diagnostic prediction based on the first 3D mask and the second 3D mask.

10. The method of claim 9, wherein capturing the input data from the imaging device includes capturing a cone-beam computer tomography (CBCT) scan of the patient.

11. The method of claim 10, wherein capturing the CBCT scan of the patient includes capturing an image of an airway of the patient.

12. The method of claim 11, further comprising displaying the diagnostic prediction on a display as a 3D overlay of the airway of the patient.

13. The method of claim 11, wherein determining the diagnostic prediction includes training a second machine learning network to generate at least one prediction regarding a diameter of the airway of the patient.

14. The method of claim 9, wherein generating the first 3D mask includes generating a 3D segmentation mask.

15. The method of claim 14, wherein generating the 3D segmentation mask includes training a first machine learning network to extract at least one feature from the input data through a plurality of convolutional layers.

16. The method of claim 15, wherein extracting the at least one feature from the input data includes downsampling to extract high-level features from the input data.

17. A non-transitory computer readable storage medium including instructions that, when executed by a computer, cause the computer to perform a method for image analysis, the method comprising:
capturing input data from an imaging device, the input data including a three-dimensional (3D) image of a portion of a patient;
receiving the input data from the imaging device;
generating a first 3D mask based on the input data;
generating a second 3D mask based on the first 3D mask, wherein generating the second 3D mask includes generating a patient-specific 3D segmentation mask by:
predicting a plurality of two-dimensional (2D) slices based on the first 3D mask, wherein each 2D slice of the plurality of 2D slices is an axial cross-section of the first 3D mask;
generating a measurement profile for each 2D slice of the plurality of 2D slices by determining a maximum diameter and a minimum diameter of a portion of each 2D slice; and
assigning a label to each 2D slice of the plurality of 2D slices based on a predetermined threshold, wherein the predetermined threshold is based on a thickness of a cross-section of the measurement profile; and
determining a diagnostic prediction based on the first 3D mask and the second 3D mask.

* * * * *